（12） United States Patent
Whipple et al.

(10) Patent No.: US 9,055,986 B1
(45) Date of Patent: Jun. 16, 2015

(54) ORTHOPEDIC FASTENER

(71) Applicants: Dale Whipple, Acworth, GA (US);
Kenneth Richard Barra, Acworth, GA (US)

(72) Inventors: Dale Whipple, Acworth, GA (US);
Kenneth Richard Barra, Acworth, GA (US)

(73) Assignee: Amendia, Inc., Marietta, GA (US)

( * ) Notice: Subject to any disclaimer, the term of this patent is extended or adjusted under 35 U.S.C. 154(b) by 0 days.

(21) Appl. No.: 14/538,860

(22) Filed: Nov. 12, 2014

Related U.S. Application Data

(63) Continuation-in-part of application No. 14/156,782, filed on Jan. 16, 2014.

(51) Int. Cl.
*A61B 17/86* (2006.01)
*F16B 35/04* (2006.01)

(52) U.S. Cl.
CPC ............... *A61B 17/863* (2013.01); *F16B 35/04* (2013.01)

(58) Field of Classification Search
CPC ............................. A61B 17/863; F16B 35/04
See application file for complete search history.

(56) References Cited

U.S. PATENT DOCUMENTS

| | | | |
|---|---|---|---|
| 2,382,019 A | 8/1945 | August | |
| 5,593,410 A | 1/1997 | Vrespa | |
| 5,601,553 A | 2/1997 | Trebing | |
| 6,030,162 A | 2/2000 | Huebner | |
| 6,565,573 B1 | 5/2003 | Ferrante | |
| 8,075,604 B2 | 12/2011 | Denis et al. | |
| 8,333,590 B2 | 12/2012 | Hansson | |
| 8,348,573 B2 * | 1/2013 | Chang | ............ 411/387.1 |
| 8,419,779 B2 | 4/2013 | Rinner | |
| 2012/0178048 A1 | 7/2012 | Cottrell | |
| 2013/0218213 A1 | 8/2013 | Lemoine | |
| 2014/0142636 A1 | 5/2014 | Hes | |

FOREIGN PATENT DOCUMENTS

WO    2013068088    5/2013

* cited by examiner

*Primary Examiner* — Andrew Yang

(74) *Attorney, Agent, or Firm* — David L. King

(57) ABSTRACT

An orthopedic fastener has a head and a shank. The shank has a leading end portion adjacent a distal tip and a trailing end portion adjacent a head. An intermediate transition is positioned between the leading and trailing end portions. At the intermediate transition, the shank increases in diameter. The leading end portion has a first thread which optionally may include one or more self-tapping cutting grooves extending adjacent the distal tip and through a plurality of the first threads. The trailing end portion has second threads extending toward the head from the intermediate transition. The second threads of the trailing end portion are larger in outer diameter than the first threads in the leading end portion. The intermediate transition has one or more cutting grooves traversing the increasing diameter.

18 Claims, 4 Drawing Sheets

ORTHOPEDIC FASTENER

RELATED APPLICATIONS

This application is a continuation in part of U.S. Ser. No. 14/156,782 filed Jan. 16, 2014 entitled "Improved Orthopedic Fastener".

TECHNICAL FIELD

The present invention relates generally to bone fasteners, more particularly to an improved orthopedic fastener with an improved thread cutting feature to secure the fastener in bone

BACKGROUND OF THE INVENTION

In orthopedic bone repair procedures, a variety of devices and implants have been devised to stabilize a bone fracture or to space vertebrae or attach ligaments or tendons to bone.

Most of these devices require the use of threaded fasteners or screws that are driven into the bone and held or anchored in place to the bone.

The bone structure typically has a hard outer surface or shell commonly referred to as cortical bone and a softer interior of a more open celled spongy structure of cancellous bone. Accordingly, the fastener must be held in place taking into account the structure of the bone.

A variety of unique thread configurations for bone screws have been developed for this purpose, the goal being to provide a safe and reliable fastening into the bone material.

The present invention provides a unique and advantageous design to create secure attachment of a bone fastener. Loosening of the fastener and damaging the threads cut into the bone are primary limitations of prior art fasteners.

These and other limitations in the prior art have been corrected and solved by the present invention as disclosed herein.

SUMMARY OF THE INVENTION

An orthopedic fastener has a head and a shank. The shank extends from the head to a distal tip. The shank has a leading end portion adjacent the distal tip and a trailing end portion adjacent the head. An intermediate transition is positioned between the leading and trailing end portions. At the intermediate transition, the shank increases in diameter. The leading end portion has a first thread which optionally may include one or more self-tapping cutting grooves extending adjacent the distal tip and through a plurality of the first threads. The trailing end portion has second threads extending toward the head from the intermediate transition. The second threads of the trailing end portion are larger in outer diameter than the first threads in the leading end portion. The intermediate transition has one or more cutting grooves traversing the increasing diameter. Preferably, the intermediate transition has the one or more second cutting groove extending from at least a first thread in the intermediate transition through at least one of said second threads to initiate tapping of the larger diameter threads of the trailing end portion into cortical bone. The optional first cutting grooves, if used, and the one or more cutting grooves in the intermediate transition, in combination with the threads form threads in the bone to hold the fastener, the first threads being positioned in cancellous bone and the second threads in harder cortical bone on insertion.

The first thread can have a pitch equal to said second thread. In one embodiment, the first thread has a pitch equal that of the larger diameter second thread and the first thread extends between the distal end portion increasing in diameter at the intermediate transition to equal the diameter of the second threads toward the head through the trailing end portion and the second thread extends helically spiraled between the first threads.

The orthopedic fastener wherein the self-tapping one or more cutting grooves allow for the combination of the first and second threads in the trailing end portion to cut increasing the diameter of first threads previously formed in the bone and creating the larger cut second formed threads without damaging the bone threads and wherein a recess may be positioned between the head and the end of the threads in the trailing end portion. The orthopedic fastener can be an implantable metal. The implantable metal can be one of titanium, stainless steel or cobalt chrome.

BRIEF DESCRIPTION OF THE DRAWINGS

The invention will be described by way of example and with reference to the accompanying drawings in which.

DETAILED DESCRIPTION OF THE INVENTION

Figure 1:
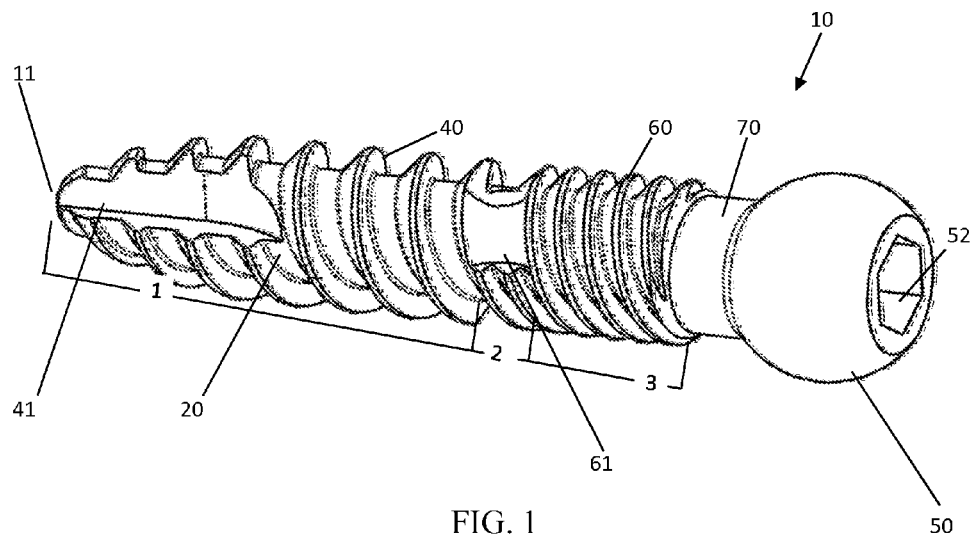
FIG. 1 is a perspective view of a bone screw or orthopedic fastener according to one embodiment of this invention.
Figure 2:
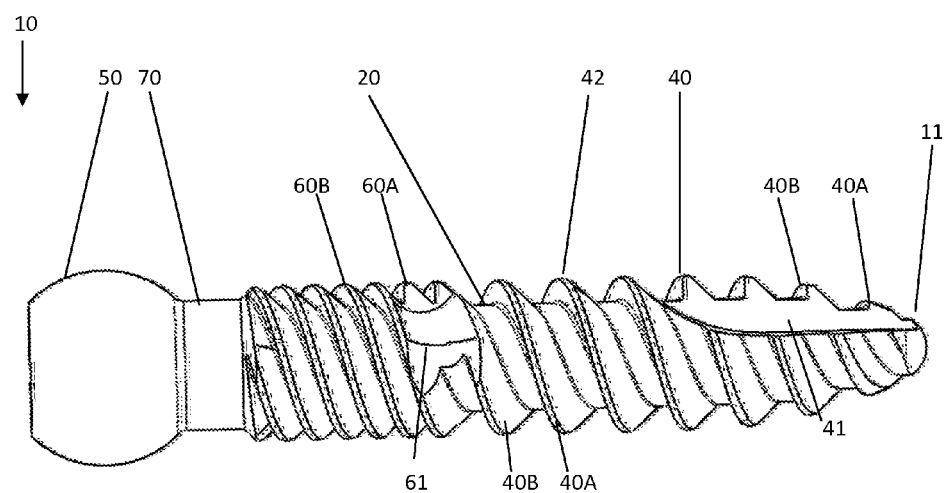
FIG. 2 is a side view of the fastener of FIG. 1.
Figure 3:
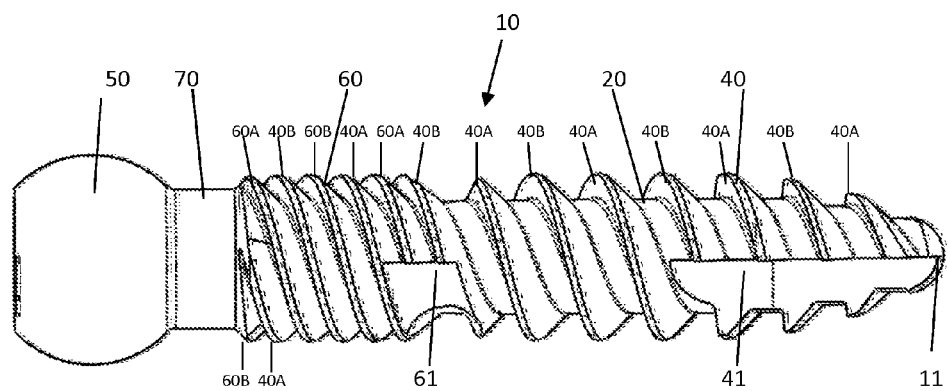
FIG. 3 is a top plan view of the fastener of FIG. 1.

Generally, an orthopedic fastener of this invention includes a head and a shank extending from the screw head to a distal tip. As used herein the term "head" means any head or top end of a fastener. The screw shank has trailing end portion including a recess adjacent to the head of the fastener, an intermediate transition section, and a leading end portion adjacent to the distal tip. In at least one embodiment, the fastener also includes a substantially continuous thread along at least a portion of the shank which extends radially outward from the shank.

The fastener of this invention is adapted to be used alone or in conjunction with a system for use in repairing a bone fracture or in fixing an orthopedic implant in a patient. The fastener can be used alone to aid in the reduction of small bone fractures. Additionally, a fastener according to this invention can be used in conjunction with an orthopedic implant to fix the implant securely to the skeletal system of the patient.

FIGS. 1 through 5 depict one embodiment of a fastener 10 according to this invention. As shown in the figures, orthopedic fastener 10 includes a head 50 and a shank 20. Preferably, head 50 is adapted to contact the bone. The shank 20 extends from head 50 to a distal tip 11. A continuously extending first thread 40 extends evenly about the outer surface of the shank 20. The leading end portion adjacent distal tip 11 includes a fluted groove 41 for the removal of bone chips as the fastener 10 is implanted into the bone. Tip 11 of the fastener 10 is a self-tapping, non-self-drilling tip with a generally conical configuration with a foreshortened end, e.g. a frusto-conical tip.

Preferably, fastener 10 is a self-tapping, non-self-drilling bone screw so that tip 11 requires a predrilled hole before insertion into the bone and only first threads 40 of fastener 10 initially cut into the bone. The pitch of the threads 40 at tip 11 should be sufficiently small to advance the fastener 10 at a rate which allows tip 11 to advance into the bone, but sufficiently large to provide adequate bone purchase and to minimize the number of turns required to seat the fastener 10. A suitable pitch for threads 40 may be in the range of about 5 threads-per-inch to about 50 threads-per-inch.

In the preferred embodiment, the first threads 40 use a double start 40A, 40B thread with a high helix angle. Each is shown 180 degrees at the distal tip 11. At the trailing end portion 3 and the intermediate transition 2, the second threads 60 are also a double or two start thread 60A, 60B. This combination at the intermediate transition 2 initiates the additional two starts so the fastener 10 has four starts 40A, 40B and 60A, 60B as illustrated.

Each thread start preferably has one cutting groove. These cutting grooves are positioned at the beginning of each thread start. Accordingly, when there are two starts there are two cutting grooves spaced 180 degrees apart. This is as shown in the exemplary embodiment. Had three thread starts been employed, there would be three cutting grooves. In the present invention, the second set of threads has two starts so the fastener 10 has four cutting grooves, a first pair at the distal end and a second pair at the intermediate transition. In the illustrated embodiments, the second pair of cutting grooves are shown aligned with the first pair. This is a simple design preference since the two second thread starts could be at any location, the second pair of cutting grooves could be at any angle or location relative to the first pair. The important thing is each thread start within a pair in the present invention is 180 degrees apart. So the cutting grooves are 180 degrees apart in the transition 2 and similarly 180 degrees in the leading end portion 1 and, as shown, the intermediate grooves are aligned with the leading grooves along the shank. Alternatively, the starts and grooves relative to another section or end could be positioned at any angle relative to the other end or section. This is possible due to the second threads being started in a spaced location removed from the leading end portion 1 and distal tip 11 in the intermediate transition section 2.

The length of the fastener 10 should be adapted to correspond to the use. The fastener 10 can be any suitable length; preferably, the length of the fastener 10 is generally from about 20 mm to about 160 mm. More preferably, the length of fastener 10 is from about 30 mm to about 65 mm; preferably, the length of the shank 20 is approximately 4 to 6 mm less than the total length of the fastener, depending on the head shape and length.

Figure 4:
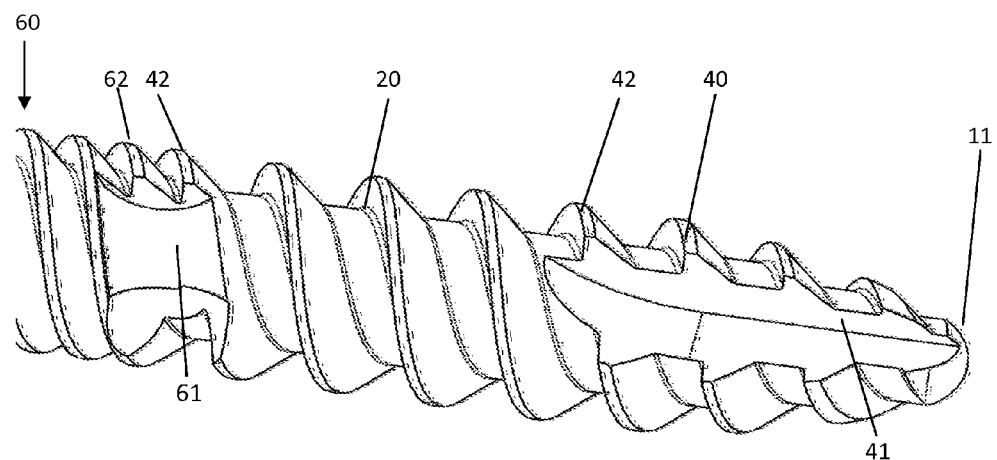
FIG. 4 is a partial perspective view of the fastener of FIG. 1.
Figure 5:
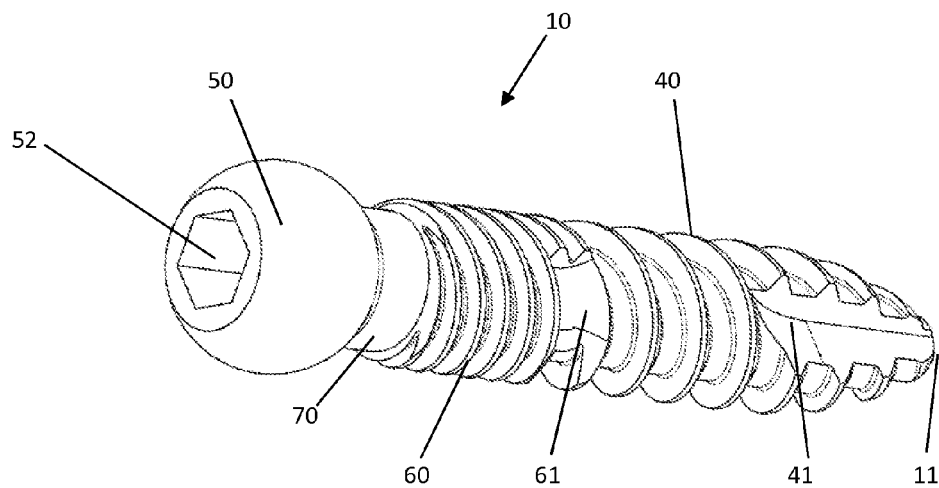
FIG. 5 is a perspective view of the head and internal surface of the fastener head of the fastener.

FIG. 4 is a side view of the fastener 10 of FIG. 1 and shows the detailed characteristics of the shank 20 and thread 40 of fastener 10. Shank 20 has a minor diameter and the first thread 40 a major diameter 42, defined by the diameter of the first thread 40. The thread height is equal to one half of the difference between the minor diameter and the major diameter 42. The difference is divided by two to account for the thread height on either side of the shank 20. Alternatively, the major diameter can be described as the sum of the minor shank diameter and twice the thread height. Note that shank minor diameter and thread major diameter and thread height can vary along the length of the fastener, as described below.

Shank 20 has three sections: trailing end portion 3; intermediate transition or section 2; and leading end portion 1. Trailing end portion 3 is the portion of the shank 20 adjacent to head 50, leading end portion 1 is the portion of the shank 20 adjacent to the frusto-conical distal tip 11, and intermediate section 2 is the portion of the shank 20 between the leading and trailing end portions. Each shank section has a minor shank diameter which may or may not remain constant from one section to another or within a section itself. Thus, trailing end portion has a first minor diameter, intermediate section as a second minor diameter, and leading end portion has a third minor diameter.

Intermediate section 2, of the embodiment shown in FIGS. 1-6, has a generally cylindrical geometry with a substantially constant minor diameter. The minor diameter can be any suitable length adapted to the size and function of the fastener. Preferably, the second minor diameter of the fastener 10 of the present invention is generally from about 6.0 mm to about 3.5 mm, more preferably from about 5.5 mm to about 4.0 mm, and most preferably from about 5.0 mm to about 4.5 mm.

In the embodiment shown, leading end portion 1 includes a taper or curvature extending from the end of the intermediate section 2 to the tip 11 at an angle theta θ or radius of curvature. Theta θ angle may also be any suitable angle, and is generally from about 1 degree to about 8 degrees, and preferably from about 1 degree to about 3 degrees. Thus, leading end portion 1 has a generally tapered geometry such that the minor diameter decreases from the section adjacent to intermediate section 2 in the direction of tip 11. The taper narrows towards the tip of the fastener 10 creating a frusto-conical tip area. The curvature has a radius or multiple radii to form a narrowing bullet like shape. This narrowing shape at the tip 11 end allows the fastener 10 to follow the pre-drilled hole more effectively and to advance more easily into the bone and through an aperture in an orthopedic implant.

Additionally, the first thread 40, thread height, and major diameter of a fastener 10 of this invention may vary along the length of the fastener body. As with the minor diameter, each shank section 1, 2 or 3 has a corresponding thread section and major diameter defined by the relative thread height.

First threads 40 extend in intermediate section 2 and have a substantially constant thread height due to the substantially constant second minor diameter of shank 20 and second major diameter in intermediate section 2. The major diameter of the thread is suited to the size of the fastener 10 and the intended function; preferably, the major diameter is from about 4.5 mm to about 8.5 mm, more preferably from about 5.5 mm to about 7.5 mm. Additionally, the ridge top of intermediate thread section can be relatively broad and wide as if the pointed end has been shaved off. This flat ridge top can be useful in the soft trabecular region of the bone where the leading end portion 1 and the intermediate section 2 will reside. The flat ridge top and constant minor diameter of the intermediate section also suit a fastener adapted for insertion through an aperture in an orthopedic implant for fixing the implant to the skeletal system of a patient.

Taper on leading end portion 1 results in a decreasing minor diameter, but the third major thread diameter is the same as second major thread diameter in the intermediate section 2 and trailing section 3. The substantially constant major diameter through intermediate section 2 and trailing end portion 3 results in a thread height of the threads along leading end portion 1 that is greater than the thread height of threads in intermediate section 2 and the trailing end portion 3. This increased thread height provides a better "bite" or grasp into the bone and more effectively draws the fastener 10 into the bone. The ridge top in this leading end portion 1 can be narrow, or pointy, for better pull through and purchase, particularly on the far cortex of the bone. The cortex, unlike the trabecula, is hard and provides strength to the bone, and thus requires a stronger grasp.

In trailing end portion 3 the thread heights 42, 62 of first and second threads 40, 60 are the same or slightly less than thread height 42 of the first threads 40 in the intermediate transition section 2 because both the minor shank diameter and the major thread diameter increase or stay the same along no taper or a slight taper in the direction of the head 50. A space is left between the threads and the head 50 providing room for a recess 70. This recess 70 can have an enlarged shank diameter for increased strength, and a tight wedge fit of the trailing end portion 3 of the fastener 10. The ridge top of threads 40, 60 along trailing end portion 3 is also generally narrow and pointy to provide for better seating of the fastener 10 and better purchase in the hard bone material of the near cortex.

The dual tapers, and an increased height of threads 40, 60 on the intermediate section 2 and trailing end portion 3 of fastener 10 provides improved purchase on both the near and far cortex of the bone. Intermediate section 2 with its second cutting groove 61 does not require a tapered geometry or a high thread height because it can lie in and occupy the inner portion of the bone with trabecular bone tissue, a softer, spongy bone tissue, and optionally occupies the interior of an aperture in an orthopedic implant when the fastener is used for fixing an orthopedic implant in a patient.

As discussed above, the trailing end portion 3 of shank 20 has an enlarged minor diameter to provide structural reinforcement for the recess 70 adjacent the head 50. In one embodiment of the invention, the head 50 includes a geometrically shaped socket 52 adapted to engage a corresponding driver and an axial bore extending from the bottom of the socket 52 into the upper portion of the fastener shank 20. The bore can include a connecting structure that corresponds to connecting structure on the driver. The connecting structure may be any suitable structure that couples the fastener to the driver, such as threads, or a snap ring. The orthopedic fastener can be an implantable metal. The implantable metal can be one of titanium, stainless steel or cobalt chrome.

Figure 6:
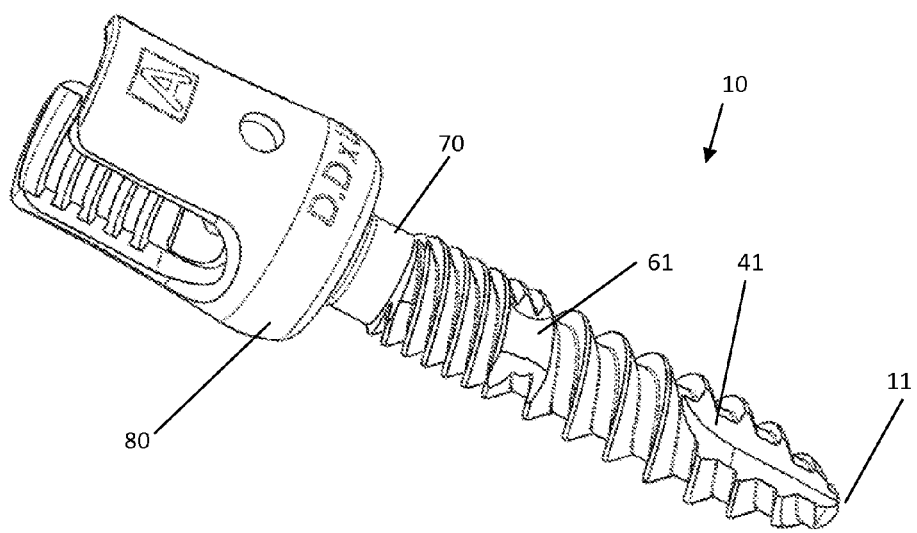
FIG. 6 is a view of the fastener of the present invention with a tulip attached.

As shown in FIG. 6, the fastener 10 can be used with a tulip 80.

Figure 7:
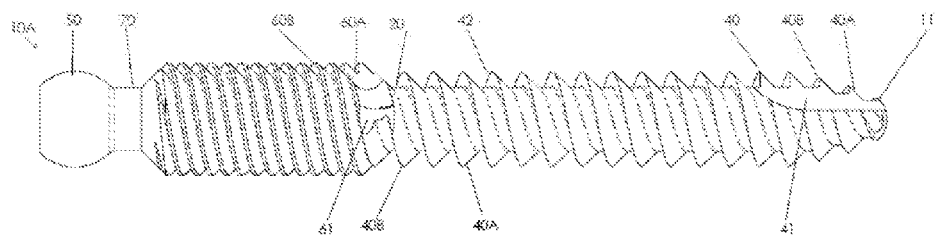
FIG. 7 is a side view of the bone screw or orthopedic fastener of a second embodiment having a stepped up dual diameter configuration.
Figure 8:
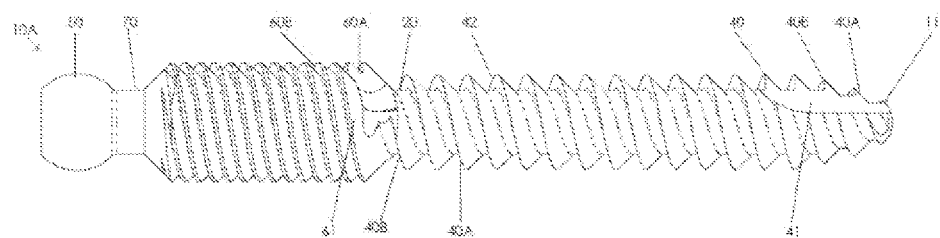
FIG. 8 is a side view of a different sized second embodiment of the present invention.

With reference to FIGS. 7 and 8, orthopedic fastener 10A is illustrated. Fastener 10A has all the features of fastener 10 and those common elements are marked accordingly with the same reference numerals. A key distinction of the fastener 10A is the trailing end portion second threads have a stepped up larger outer diameter. This increased diameter initiates in an intermediate section or transition region 2. The shank 20 increases in diameter, preferably rather smoothly in a conical fashion as the first threads in this region 2 similarly increase in outer diameter. As shown, the fastener 10A has cutting grooves 61 in this stepped up diameter intermediate section transition region 2. These cutting grooves 61 allow the fastener to either enlarge the bone formed threads created by the first threads 40 on entry or can cut these bone threads away to accommodate the larger threads 60 in the trailing portion.

As previously discussed, the first thread 40 can be helically intertwined with the second thread 60, but in this second embodiment, the fastener 10A has the first thread 40 increase in outer diameter through the transition region 2 to the same enlarged diameter of the second thread 60. As with the first embodiment, the trailing end portion 2 threads 60 are ideal for fastening into the hard cortical bone while the leading end portion 1 threads 40 will fasten into the softer cancellous bone.

Optionally, the leading end portion 1 adjacent the tip 11 can also have cutting grooves 41. In some cases, a surgeon may want to pre-drill the bone making initial entry self-tapping first thread 40 optional or unnecessary; however, on fastening to bone, the cutting grooves 61 in the intermediate transition region 2 enlarges the bone thread to accommodate the larger second threads 60 and can be fashioned to insure a very tight fit without fracturing the cortical bone. This insures the bone fastener 10A fits more securely to the bone without damaging the underling bone first threads in the cancellous bone region. This increase in thread diameters preferably is kept within 1 to 2.0 mm, a 1 mm thread increase in small sizes like 6.5 min to 7.5 mm and a larger increase in size from the 8.5 mm to 10 mm are easily accommodated. The overall length of the screws is typically 20 mm to 40 mm with the trailing threads being less than half the total length, typically 30 percent to about 25 percent of the total threaded length. This reflects the bone structure having a rather thin depth in the hard cortical bone compared to the softer cancellous bone into which the fastener 10A is attached. It is understood the sizes and dimensions can be varied to reflect specific orthopedic applications.

Variations in the present invention are possible in light of the description of it provided herein. While certain representative embodiments and details have been shown for the purpose of illustrating the subject invention, it will be apparent to those skilled in this art that various changes and modifications can be made therein without departing from the scope of the subject invention. It is, therefore, to be understood that changes can be made in the particular embodiments described, which will be within the full intended scope of the invention as defined by the following appended claims.

What is claimed is:

1. An orthopedic fastener comprising:
   a head;
   a shank, the shank extending from the head to a distal tip, the shank having a leading end portion adjacent the distal tip and a trailing end portion adjacent the head and an intermediate transition positioned between the leading and trailing end portions, at the intermediate transition the shank increasing in diameter to a larger diameter; and
   wherein the leading end portion has a first thread extending adjacent the distal tip through to at least the intermediate transition, and the trailing end portion has a second thread extending toward the head from the intermediate transition, the second thread of the trailing end portion being larger in outer diameter than the first threads in the leading end portion, the intermediate transition having one or more cutting grooves extending from at least a first thread in the intermediate transition through at least one of said second threads to initiate tapping of the second threads into cortical bone, and wherein the one or more cutting grooves in combination with the threads form threads in the bone to hold the fastener, the first thread has a pitch equal that of the second thread and the first thread extends between the distal end to the head, the first thread increasing in outer diameter at the intermediate transition.

2. The orthopedic fastener of claim 1 wherein the second thread extends helically spiraled between the first threads in the trailing end portion.

3. The orthopedic fastener of claim 1 wherein the self-tapping one or more cutting groove allows the larger diameter threads in the trailing end portion to pass through by enlarging or cutting away first threads previously formed at an outer cortical region in the bone to accommodate larger diameter of the second threads to form a larger sized bone thread.

4. The orthopedic fastener of claim 1 wherein a recess is positioned between the head and the trailing end portion.

5. The orthopedic fastener of claim 1 is an implantable metal.

6. The orthopedic fastener of claim 5 wherein the implantable metal is one of titanium, stainless steel or cobalt chrome.

7. The orthopedic fastener of claim 1 further comprises a tulip affixed to the head.

8. The orthopedic fastener of claim 1 wherein the second thread has a pitch half the pitch of the first thread.

9. The orthopedic fastener of claim 8 wherein the first thread has a height greater as measured from the shank to an outer thread diameter in the leading end portion than a height of second thread in the trailing end portion.

10. The orthopedic fastener of claim 1 wherein the fastener has a threaded length of at least 20 mm.

11. The orthopedic fastener of claim 1 wherein the trailing end portion threads extend less than 30 percent the total threaded length.

12. The orthopedic fastener of claim 1 wherein the leading end portion has one or more cutting grooves adjacent the distal tip and extending from at least a first thread in the leading end portion.

13. An orthopedic fastener comprising:
a head;
a shank, the shank extending from the head to a distal tip, the shank having a leading end portion adjacent the distal tip and a trailing end portion adjacent the head and an intermediate transition positioned between the leading and trailing end portions, at the intermediate transition the shank increasing in diameter to a larger diameter; and
wherein the leading end portion has a first thread extending adjacent the distal tip through to at least the intermediate transition, and the trailing end portion has a second thread extending toward the head from the intermediate transition, the second thread of the trailing end portion being larger in outer diameter than the first threads in the leading end portion, the intermediate transition having one or more cutting grooves extending from at least a first thread in the intermediate transition through at least one of said second threads to initiate tapping of the second threads into cortical bone, and wherein the one or more cutting grooves in combination with the threads form threads in the bone to hold the fastener, wherein the first threads at the leading end portion are of a size 6.5 mm and the second threads at the trailing end portion are 7.5 mm, the intermediate transition increasing by 1.0 mm.

14. An orthopedic fastener comprising:
a head;
a shank, the shank extending from the head to a distal tip, the shank having a leading end portion adjacent the distal tip and a trailing end portion adjacent the head and an intermediate transition positioned between the leading and trailing end portions, at the intermediate transition the shank increasing in diameter to a larger diameter; and
wherein the leading end portion has a first thread extending adjacent the distal tip through to at least the intermediate transition, and the trailing end portion has a second thread extending toward the head from the intermediate transition, the second thread of the trailing end portion being larger in outer diameter than the first threads in the leading end portion, the intermediate transition having one or more cutting grooves extending from at least a first thread in the intermediate transition through at least one of said second threads to initiate tapping of the second threads into cortical bone, and wherein the one or more cutting grooves in combination with the threads form threads in the bone to hold the fastener, wherein the first threads at the leading end portion are of a size 8.5 mm and the second threads at the trailing end portion are 10 mm, the intermediate transition increasing by 1.5 mm.

15. An orthopedic fastener comprising:
a head;
a shank, the shank extending from the head to a distal tip, the shank having a leading end portion adjacent the distal tip and a trailing end portion adjacent the head and an intermediate transition positioned between the leading and trailing end portions, at the intermediate transition the shank increasing in diameter to a larger diameter; and
wherein the leading end portion has a first thread with one or more self-tapping cutting grooves extending adjacent the distal tip through a plurality of the first threads, the first thread extending to at least the intermediate transition, and the trailing end portion has a second thread extending toward the head from the intermediate transition, the second thread of the trailing end portion being larger in outer diameter than the first threads in the leading end portion, the intermediate transition having one or more second cutting grooves extending from at least a first thread in the intermediate transition through at least one of said second threads to initiate tapping of the second threads into cortical bone, and wherein the one or more cutting grooves in combination with the threads form threads in the bone to hold the fastener.

16. The orthopedic fastener of claim 15 wherein the first thread has a pitch equal that of the second thread.

17. The orthopedic fastener of claim 16 wherein the first thread extends between the distal end to the head, the first thread increasing in outer diameter at the intermediate transition.

18. The orthopedic fastener of claim 17 wherein the second thread extends helically spiraled between the first threads in the trailing end portion.

* * * * *